United States Patent [19]

Eidenschink et al.

[11] 4,330,426
[45] May 18, 1982

[54] CYCLOHEXYLBIPHENYLS, THEIR PREPARATION AND USE IN DIELECTRICS AND ELECTROOPTICAL DISPLAY ELEMENTS

[75] Inventors: Rudolf Eidenschink, Dieburg; Dietrich Erdmann, Mühltal; Joachim Krause, Dieburg; Ludwig Pohl, Darmstadt, all of Fed. Rep. of Germany

[73] Assignee: Merck Patent Gesellschaft mit beschränkter Haftung, Darmstadt, Fed. Rep. of Germany

[21] Appl. No.: 166,663

[22] Filed: Jul. 7, 1980

[30] Foreign Application Priority Data

Jul. 6, 1979 [DE] Fed. Rep. of Germany ....... 2927277

[51] Int. Cl.³ ................... G02F 1/13; C09K 3/34; C07C 13/28; C07C 21/24; C07C 43/205; C07C 69/017
[52] U.S. Cl. .................. 252/299.63; 252/299.5; 350/350 R; 350/350 S; 560/141; 568/642; 570/129; 585/25; 585/20
[58] Field of Search ............ 570/129; 560/141; 568/642; 585/25, 20; 252/299.5, 299.63, 299.66; 350/350 R, 350 S

[56] References Cited

U.S. PATENT DOCUMENTS

| | | | |
|---|---|---|---|
| 3,517,069 | 6/1970 | Bach et al. .................... | 568/642 |
| 3,960,752 | 6/1976 | Flanderman ................ | 252/299.67 |
| 4,011,173 | 3/1977 | Steinstrasser ................ | 252/299.5 |
| 4,118,335 | 10/1978 | Krause et al. ................ | 252/299.5 |
| 4,130,502 | 12/1978 | Eidenschink et al. ........ | 252/299.63 |
| 4,154,697 | 5/1979 | Eidenschink et al. ........ | 252/299.63 |
| 4,180,475 | 12/1979 | Schadt et al. ................ | 252/299.5 |
| 4,181,625 | 1/1980 | Eidenschink et al. ........ | 252/299.63 |
| 4,198,130 | 4/1980 | Boller et al. .................. | 252/299.5 |
| 4,228,029 | 10/1980 | Osman ......................... | 252/299.5 |
| 4,229,315 | 10/1980 | Krause et al. ................ | 252/299.63 |

FOREIGN PATENT DOCUMENTS 2031010 4/1980 United Kingdom .......... 252/299.67

OTHER PUBLICATIONS

Billard, J., et al., Mol. Cryst. Liq. Cryst., vol. 41 (Letters), pp. 217–222 (1978).

*Advances in Liquid Crystal Research and Applications*, Bath, L., Proceedings of Third L. C. Conf. of Socialist Countries, Budapest, Aug. 27–31 (1979), vol. 2, pp. 997–1002 Pergamon Press, N.Y. (1981).

*Primary Examiner*—Teddy S. Gron
*Attorney, Agent, or Firm*—Millen & White

[57] ABSTRACT

Compounds of the formula

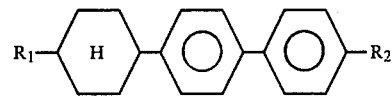

wherein $R_1$ is alkyl of 1–12 C atoms and $R_2$ is an optionally perfluorinated alkyl, alkoxy or alkanoyloxy group, each of 1–12 C atoms are valuable liquid crystalline components for broadening the mesophase temperature range of liquid crystalline dielectrics having negative dielectric anisotropy.

7 Claims, No Drawings

CYCLOHEXYLBIPHENYLS, THEIR PREPARATION AND USE IN DIELECTRICS AND ELECTROOPTICAL DISPLAY ELEMENTS

BACKGROUND OF THE INVENTION

For electrooptical display elements, the properties of nematic or nematic-cholesteric liquid crystal materials, which significantly change their optical properties, such as light absorption, light scattering, double refraction, reflecting power or color, under the influence of electric fields, are utilized to an increasing extent. The functioning of such display elements is based, for example, on the phenomena of dynamic scattering, the deformation of aligned phases, the Schadt-Helfrich effect in a twisted cell or the cholesteric-nematic phase transition.

Industrial application of these effects in electronic components necessitates liquid crystal dielectrics which must fulfill a large number of requirements. Chemical stability towards moisture, air and physical influences, such as heat, radiation in the infrared, visible and ultra-violet ranges and constant and alternating electrical fields, is particularly important in this context. A liquid crystal mesophase in the temperature range from at least $+10°$ C. to $+50°$ C., preferably from $0°$ C. to $60°$ C., and as low as possible a viscosity at room temperature, which should preferably be not more than $70.10^{-3}$ Pa.s, are also required of liquid crystal dielectrics which can be used industrially. Finally, these dielectrics must exhibit no characteristic absorption in the range of visible light, i.e., they must be colorless.

A number of liquid crystal compounds which fulfill the stability requirements demanded of dielectrics for electronic components and which are also colorless are already known. These include, in particular, the p,p'-disubstituted phenyl benzoates described in German Offenlegungsschrift No. 2,139,628 and the p,p'-disubstituted phenylcyclohexane derivatives described in German Offenlegungsschrift No. 2,636,684. In both these classes of compounds, and also in other known series of compounds having a liquid crystal mesophase, there are no individual compounds which form a liquid crystal nematic mesophase in the required temperature range of $10°$ C. to $60°$ C. Mixtures of two or more compounds are, thus, as a rule prepared in order to obtain substances which can be used as liquid crystal dielectrics. These are usually obtained by mixing at least one compound having a low melting point and clear point with another compound having a significantly higher melting point and clear point.

A mixture which has a melting point below that of the lower-melting component, while the clear point is between the clear points of the components, is usually obtained by this procedure. However, optimum dielectrics cannot be prepared in this manner, since the components with the high melting points and clear points almost always also impart a high viscosity to the mixtures. The switching times of the electrooptical display elements produced with these mixtures are thus undesirably lengthened.

It has thus been sought to prepare liquid crystal dielectrics which have a nematic phase in the required temperature range and which provide sufficiently short switching times in liquid crystal cells at room temperature.

Hexahydroterphenyl derivatives satisfying these requirements can be achieved for the range of liquid crystal dielectrics having positive dielectric anisotropy as disclosed in German Offenlegungsschrift No. 2,701,591 or its equivalent U.S. Pat. No. 4,154,697. However, these hexahydroterphenyl derivatives cannot be used to prepare liquid crystal dielectrics having negative dielectric anisotropy, which, for example, are required for liquid crystal display elements which operate by the principle of dynamic scattering.

SUMMARY OF THE INVENTION

Accordingly, it is an object of this invention to provide liquid crystalline compounds having such properties.

Upon further study of the specification and appended claims, further objects and advantages of this invention will become apparent to those skilled in the art.

These objects have been achieved by providing cyclohexylbiphenyls of formula (I)

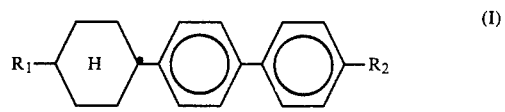

wherein $R_1$ is alkyl of 1–12 C atoms and $R_2$ is optionally perfluorinated alkyl, alkoxy or alkanoyloxy of 1–12 C atoms.

The present invention thus relates to the cyclohexylbiphenyls of formula (I), processes for their preparation and their use as components of liquid crystal dielectrics. The invention furthermore relates to liquid crystal dielectrics containing at least one cyclohexylbiphenyl derivative of formula (I) and to electrooptical display elements based on a liquid crystal cell containing such a liquid crystal dielectric.

DETAILED DISCUSSION

The compounds of this invention are outstandingly suitable as components of mixtures for liquid crystal dielectrics. Surprisingly, the compounds of formula (I) themselves have liquid crystal mesophases within a broad temperature range, the clear points being as a rule about $150°$ C. or more. These broad mesophases are especially surprising in view of the structure of the cyanosub- stituted hexahydroterphenyl derivatives according to German Offenlegungsschrift No. 2,701,591. This is shown, for example, by a comparison of the liquid crystal cyanobiphenyl derivatives according to German Offenlegungsschrift No. 2,356,085 with the known p,p'-dialkyl- and -alkyl-alkoxy-biphenyls, which are not liquid crystalline.

The dielectric anisotropy of the cyclohexylbiphenyls of formula (I) is between about $-1$ and $+3$, and as a rule is about zero. The temperature range of the mesophase of liquid crystal base materials is significantly widened by adding these compounds; in many cases, surprisingly, the viscosities of liquid crystal materials which in themselves have a relatively low viscosity are also reduced further.

The substituent $R_1$ in the compounds of formula (I) can be straight-chain or branched. If R is straight-chain, i.e., methyl, ethyl, n-propyl, n-butyl, n-pentyl, n-hexyl, n-heptyl, n-octyl, n-nonyl, n-decyl, n-undecyl or n-dodecyl, the corresponding compounds of formula (I) have, as a rule, particularly high clear points. The compounds of formula (I) in which $R_1$ is alkyl of 1–10, in particular of 2–8 C atoms are particularly preferred.

However, compounds of formula (I) with branched substituents as $R_1$ are also occasionally important, since these compounds frequently have better solubility properties in the customary liquid base mixtures. The compounds with a branched substituent $R_1$ can furthermore be prepared in an optically active form; thus, these substances are of importance as chiral doping substances. Such substituents $R_1$, which are not straight-chain, are preferably branched no more than once. Preferred branched substituents are those which contain a methyl or ethyl group in the 2- or 3- position of a relatively long carbon chain, for example 2-methylpropyl, 2-methylbutyl, 3-methylbutyl, 2-methylpentyl or 2-ethylhexyl.

These selection criteria also apply analogously to the substituent $R_2$ in the compounds of formula (I) when this substituent is alkyl. When $R_2$ is alkoxy or alkanoyloxy these criteria also apply to the alkyl portion of these groups. In addition, however, alkyl portions which are also branched in the 1-position are also of interest in these groups, so that examples of alkoxy groups $R_2$ which are also important, in addition to those derived from the abovementioned alkyl groups, include 1-methylpropoxy, 1-methylbutoxy, 1-methylpentyloxy, 1-methylhexyloxy, and 1-methylheptyloxy; isobutyryloxy and isovaleryloxy are of particular interest as branched alkanoyloxy groups.

At most only one of the substituents $R_1$ and $R_2$ in the compounds of this invention contains a branched carbon chain.

If $R_2$ is perfluorinated alkyl, alkoxy or alkanoyloxy, groups which are preferred are those which contain no more than 8 C atoms, and in particular those with 1-5 C atoms. These groups also contain at most only one chain branching, a trifluoromethyl group in the 2- or 3-position being preferred.

In all the compounds of this invention, the substituents on the cyclohexane ring are arranged in the trans-position; this is indicated in the formulae by the black marking on the right-hand side of the cyclohexane ring.

The compounds of this invention are prepared in conventional fashion for such substances. Thus, the compounds of the formula (I) wherein $R_2$ is alkyl can be obtained by reducing the carbonyl group in a compound of formula (II)

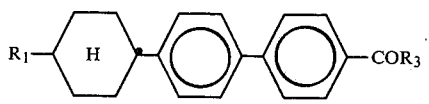

(II)

wherein $R_3$ is H or alkyl of 1-11 C atoms, to the methylene group. This reduction is carried out in a manner which is known per se, for example by catalytic hydrogenation or with hydrazine hydrate and an alkali metal hydroxide or alcoholate in a high boiling solvent, such as diethylene glycol or dimethylsulfoxide; with zinc and hydrogen chloride in diethyl ether; or with zinc amalgam in aqueous hydrochloric acid. After a working up operation which is customary per se, the compounds of formula (I) thus obtained can be purified by fractional distillation under reduced pressure or by recrystallization from a suitable solvent, for example, ethanol or ethyl acetate.

The compounds of formula (I) in which $R_2$ is alkoxy can be prepared by converting a ketone of formula (II) wherein $R_3$ is preferably methyl to a phenol of formula (II)

(III)

by treatment with an oxidizing agent and subsequent hydrolysis, and then reacting this phenol with an O-alkylating agent. The oxidizing agent used for converting the ketone (II) into the phenol (III) is, for example, performic acid or another peracid. The reaction with an O-alkylating agent, for example an alkyl iodide or alkyl bromide, is as a rule carried out in the presence of a base, such as sodium hydroxide or sodium carbonate, in a polar solvent, for example acetone.

The compounds of formula (I) in which $R_2$ is perfluoroalkyl are prepared by reacting a ketone of formula (IIa)

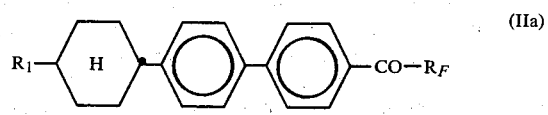

(IIa)

wherein $R_F$ is a perfluoroalkyl radical of 1-11 C atoms, with sulfur tetrafluoride. The ketones (IIa) are obtained by reacting the corresponding 4-(4-alkylcyclohexyl)-biphenyl with a perfluorocarboxylic acid halide in the presence of a Friedel-Crafts catalyst.

The compounds of formula (I) in which $R_2$ is a perfluoroalkoxy group are prepared by esterifying a phenol (III) with a perfluorocarboxylic acid under conditions which are customary per se and reacting the resulting ester with sulfur tetrafluoride in the presence of a fluorine-containing Lewis acid, for example hydrogen fluoride, boron trifluoride or titanium tetrafluoride.

The compounds of formula (I) in which $R_2$ is an optionally perfluorinated alkanoyloxy group are prepared by reacting a phenol (III) with a carboxylic acid or perfluorocarboxylic acid or a reactive derivative of such an acid, for example an acid halide, preferably an acid chloride, or an acid anhydride, advantageously in the presence of a base, such as, for example, pyridine or triethylamine.

In all the preparative reactions of this invention the starting materials have trans substituted cyclohexyl rings and the reactions proceed without inversion of configuration. Such starting materials are disclosed in U.S. Pat. No. 4,154,697.

The cyclohexylbiphenyls of formula (I) are used as components of liquid crystal dielectrics for the purpose of widening the temperature range of the liquid crystal mesophase, and in particular of raising the clear point. Compared with the benzoyloxybenzoic acid phenyl ester derivatives of German Offenlegungsschrift No. 2,139,628 or the biphenylcarboxylic acid phenyl ester derivatives or benzoic acid biphenylyl ester derivatives of German Offenlegungsschrift No. 2,450,088, which are hitherto used for this purpose, the compounds of this invention provide the considerable advantage of increasing the viscosity of the liquid crystal base dielectrics less, or even reduce it. Because of the low values of their dielectric anisotropy, they are preferably used as components of liquid crystal dielectrics having negative dielectric anisotropy.

The liquid crystal dielectrics according to this invention consist of two or more components, and among these is at least one of formula (I). The other components are preferably nematic or nematogenic substances from the classes of azobenzenes, azoxybenzenes, biphenyls, Schiff's bases, in particular benzylidene derivatives, phenyl benzoates, phenylcyclohexanes, optionally halogenated stilbenes, diphenylacetylene derivatives, diphenyl nitrones and substituted cinnamic acids. The most important compounds possible as other components of this type are characterized by formula (IV):

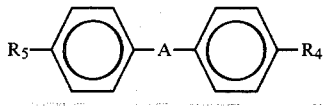
(IV)

wherein
A is

| | |
|---|---|
| —CH=CH— | —O—CO—⟨O⟩—O—CO— |
| —CX'=CH— | —CO—O—⟨O⟩—CO—O— |
| —CH=CX'— | —⟨O⟩—CO—O— |
| —C≡C— | —⟨O⟩—O—CO— |
| —N=N— | —⟨O⟩—CO—S— |
| —N(O)=N— | —⟨O⟩—S—CO— |
| —N=N(O)— | —CH=N— |
| —O—CO— | —N=CH— |
| —CO—O— | —CH=N(O)— |
| —S—CO— | —N(O)=CH— |
| —CO—S— | or a C—C single bond. |

Other possible components of the dielectrics of this invention include those compounds of formula (IV) in which one or more phenyl rings are replaced by a corresponding number of transcyclohexyl rings. X' is halogen, preferably Cl, or —CN. $R_5$ and $R_4$ are identical or different and can be alkyl, alkoxy, alkanoyl, alkanoyloxy or alkoxycarbonyloxy of up to 18, preferably up to 8, C atoms. In most of these compounds, $R_5$ and $R_4$ are preferably different, one of the radicals usually being an alkyl or alkoxy group. However, a large number of other variants of the substituents envisaged are also customary. Many such substances are commercially available.

The dielectrics according to this invention as a rule contain at least 30, preferably 50–99 and in particular 60–98, percent by weight of the compounds of formulae (I) and, if appropriate, (IV). One or more compounds of formula (I) preferably make up at least 5 percent by weight, and in most cases even 10 or more percent by weight, of this amount. The invention also comprises those liquid crystal dielectrics to which, for example, only less than 5 percent by weight, for example 0.1 to 3 percent by weight, of one or more compounds of formula (I) have been added for doping purposes.

The dielectrics of this invention are prepared in a manner which is customary per se. As a rule, the desired amount of one or more compounds of formula (I) is dissolved in the other components, preferably at elevated temperature. The completeness of the dissolving operation can be observed particularly easily if a temperature above the clear point of the base material is chosen.

However, it is also possible to mix solutions of components of formulae (I) and (IV) in a suitable organic solvent, for example acetone, chloroform or methanol, and after thorough mixing, to remove the solvent for example by distillation under reduced pressure. In this procedure, of course, care must be taken that no impurities or undesired doping substances are incorporated through the solvent.

The liquid crystal dielectrics of this invention can be modified by suitable additives so that they can be used in all types of liquid crystal display elements hitherto disclosed. Such additives are well known to those skilled in the art and are described in detail in the relevant literature. For example, it is possible to add substances to alter the dielectric anisotropy, the viscosity, the conductivity and/or the orientation of the nematic phases. Such substances are described, for example, in German Offenlegungsschriften Nos. 2,209,127, 2,240,864, 2,321,632, 2,338,281 and 2,450,088.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following example(s), all temperatures are set forth uncorrected in degrees Celsius; unless otherwise indicated, all parts and percentages are by weight.

In the examples, m. denotes the melting point and c. denotes the clear point of a liquid crystal substance in degrees Centigrade; boiling points are designated by b.p.

EXAMPLE 1

(a) 306 g of 4-(4-n-pentylcyclohexyl)-biphenyl is dissolved in a suspension of 150 g of anhydrous aluminum chloride in 2,000 ml of methylene chloride at 10°, while stirring. A solution of 79 g of acetyl chloride in 250 ml of methylene chloride is added dropwise to the solution over the course of 2 hours, while stirring. The reaction mixture is stirred for an additional 16 hours and poured into a solution of 300 ml of concentrated hydrochloric acid in 2.5 l of ice-water. The organic phase is separated off, washed with water and sodium bicarbonate solution, dried over calcium chloride and evaporated. The p-(4-n-pentylcyclohexyl)-p'-acetylbiphenyl which remains is recrystallized from ethanol; m. 125°, yield: 315 g.

(b) 175 g of p-(4-n-pentylcyclohexyl)-p'-acetylbiphenyl is dissolved in 1.5 l of tetrahydrofuran and is hydrogenated in the presence of 10 g of palladium-on-charcoal (5% of Pd) at room temperature and under normal pressure for 80 hours. The catalyst is then filtered off, the filtrate is evaporated and the p-(4-n-pentylcyclohexyl)-p'-ethylbiphenyl which remains is recrystallized from ethanol; m. 34°, c. 161°, yield: 149 g.

The following compounds are prepared analogously:
p-(4-methylcyclohexyl)-p'-methylbiphenyl,
p-(4-ethylcyclohexyl)-p'-methylbiphenyl,
p-(4-n-propylcyclohexyl)-p'-methylbiphenyl,
p-(4-n-butylcyclohexyl)-p'-methylbiphenyl,
p-(4-n-pentylcyclohexyl)-p'-methylbiphenyl, p-(4-n-hexylcyclohexyl)-p'-methylbiphenyl,
p-(4-n-heptylcyclohexyl)-p'-methylbiphenyl,
p-(4-n-octylcyclohexyl)-p'-methylbiphenyl,
p-(4-n-nonylcyclohexyl)-p'-methylbiphenyl,
p-(4-n-decylcyclohexyl)-p'-methylbiphenyl,
p-(4-n-undecylcyclohexyl)-p'-methylbiphenyl,
p-(4-n-dodecylcyclohexyl)-p'-methylbiphenyl,
p-[4-(2-methylpropyl)-cyclohexyl]-p'-methylbiphenyl,
p-[4-(2-methylbutyl)-cyclohexyl]-p'-methylbiphenyl,
p-[4-(3-methylbutyl)-cyclohexyl]-p'-methylbiphenyl and
p-[4-(2-ethylhexyl)-cyclohexyl]-p'-methylbiphenyl.
p-(4-methylcyclohexyl)-p'-ethylbiphenyl,
p-(4-ethylcyclohexyl)-p'-ethylbiphenyl,
p-(4-n-propylcyclohexyl)-p'-ethylbiphenyl,
p-(4-n-butylcyclohexyl)-p'-ethylbiphenyl,
p-(4-n-hexylcyclohexyl)-p'-ethylbiphenyl, m. 44°, c. 156°;
p-(4-n-heptylcyclohexyl)-p'-ethylbiphenyl,
p-(4-n-octylcyclohexyl)-p'-ethylbiphenyl,
p-(4-n-nonylcyclohexyl)-p'-ethylbiphenyl,
p-(4n-decylcyclohexyl)-p'-ethylbiphenyl,
p-(4-n-undecylcyclohexyl)-p'-ethylbiphenyl,
p-(4-n-dodecylcyclohexyl)-p'-ethylbiphenyl,
p-[4-(2-methylpropyl)-cyclohexyl]-p'-ethylbiphenyl,
p-[4-(2-methylbutyl)-cyclohexyl]-p'-ethylbiphenyl,
p-[4-(3-methylbutyl)-cyclohexyl]-p'-ethylbiphenyl and
p-[4-(2-ethylhexyl)-cyclohexyl]-p'-ethylbiphenyl.
p-(4-methylcyclohexyl)-p'-n-propylbiphenyl,
p-(4-ethylcyclohexyl)-p'-n-propylbiphenyl,
p-(4-n-propylcyclohexyl)-p'-n-propylbiphenyl,
p-(4-n-butylcyclohexyl)-p'-n-propylbiphenyl,
p-(4-n-pentylcyclohexyl)-p'-n-propylbiphenyl, m. 14°, c. 158°;
p-(4-n-hexylcyclohexyl)-p'-n-propylbiphenyl,
p-(4-n-heptylcyclohexyl)-p'-n-propylbiphenyl,
p-(4-n-octylcyclohexyl)-p'-n-propylbiphenyl,
p-(4-n-nonylcyclohexyl)-p'-n-propylbiphenyl,
p-(4-n-decylcyclohexyl)-p'-n-propylbiphenyl,
p-(4-n-undecylcyclohexyl)-p'-n-propylbiphenyl,
p-(4-n-dodecylcyclohexyl)-p'-n-propylbiphenyl,
p-[4-(2-methylpropyl)-cyclohexyl]-p'-n-propylbiphenyl,
p-[4-(2-methylbutyl)-cyclohexyl]-p'-n-propylbiphenyl,
p-[4-(3-methylbutyl)-cyclohexyl]-p'-n-propylbiphenyl and
p-[4-(2-ethylhexyl)-cyclohexyl]-p'-n-propylbiphenyl.
p-(4-methylcyclohexyl)-p'-n-butylbiphenyl,
p-(4-ethylcyclohexyl)-p'-n-butylbiphenyl,
p-(4-n-propylcyclohexyl)-p'-n-butylbiphenyl,
p-(4-n-butylcyclohexyl)-p'-n-butylbiphenyl,
p-(4-n-pentylcyclohexyl)-p'-n-butylbiphenyl, c. 170.5°;
p-(4-n-hexylcyclohexyl)-p'-n-butylbiphenyl,
p-(4-n-heptylcyclohexyl)-p'-n-butylbiphenyl,
p-(4-n-octylcyclohexyl)-p'-n-butylbiphenyl,
p-(4-n-nonylcyclohexyl)-p'-n-butylbiphenyl,
p-(4-n-decylcyclohexyl)-p'-n-butylbiphenyl,
p-(4-n-undecylcyclohexyl)-p'-n-butylbiphenyl,
p-(4-n-dodecylcyclohexyl)-p'-n-butylbiphenyl,
p-[4-(2-methylpropyl)-cyclohexyl]-p'-n-butylbiphenyl,
p-[4-(2-methylbutyl)-cyclohexyl]-p'-n-butylbiphenyl,
p-[4-(3-methylbutyl)-cyclohexyl]-p'-n-butylbiphenyl and
p-[4-(2-ethylhexyl)-cyclohexyl]-p'-n-butylbiphenyl.
p-(4-methylcyclohexyl)-p'-n-pentylbiphenyl,
p-(4-ethylcyclohexyl)-p'-n-pentylbiphenyl,
p-(4-n-propylcyclohexyl)-p'-n-pentylbiphenyl,
p-(4-n-butylcyclohexyl)-p'-n-pentylbiphenyl,
p-(4-n-pentylcyclohexyl)-p'-n-pentylbiphenyl, m. 13°, c. 166°;
p-(4-n-hexylcyclohexyl)-p'-n-pentylbiphenyl,
p-(4-n-heptylcyclohexyl)-p'-n-pentylbiphenyl,
p-(4-n-octylcyclohexyl)-p'-n-pentylbiphenyl,
p-(4-n-nonylcyclohexyl)-p'-n-pentylbiphenyl,
p-(4-n-decylcyclohexyl)-p'-n-pentylbiphenyl,
p-(4-n-undecylcyclohexyl)-p'-n-pentylbiphenyl,
p-(4-n-dodecylcyclohexyl)-p'-n-pentylbiphenyl,
p-[4-(2-methylpropyl)-cyclohexyl]-p'-n-pentylbiphenyl,
p-[4-(2-methylbutyl)-cyclohexyl]-p'-n-pentylbiphenyl,
p-[4-(3-methylbutyl)-cyclohexyl]-p'-n-pentylbiphenyl and
p-[4-(2-ethylhexyl)-cyclohexyl]-p'-n-pentylbiphenyl.
p-(4-methylcyclohexyl)-p'-n-hexylbiphenyl,
p-(4-ethylcyclohexyl)-p'-n-hexylbiphenyl,
p-(4-n-propylcyclohexyl)-p'-n-hexylbiphenyl,
p-(4-n-butylcyclohexyl)-p'-n-hexylbiphenyl.
p-(4-n-pentylcyclohexyl)-p'-n-hexylbiphenyl,
p-(4-n-hexylcyclohexyl)-p'-n-hexylbiphenyl,
p-(4-n-heptylcyclohexyl)-p'-n-hexylbiphenyl,
p-(4-n-octylcyclohexyl)-p'-n-hexylbiphenyl,
p-(4-n-nonylcyclohexyl)-p'-n-hexylbiphenyl,
p-(4-n-decylcyclohexyl)-p'-n-hexylbiphenyl,
p-[4-(2-methylpropyl)-cyclohexyl]-p'-n-hexylbiphenyl,
p-[4-(2-methylbutyl)-cyclohexyl]-p'-n-hexylbiphenyl,
p-[4-(2-methylbutyl)-cyclohexyl]-p'-n-hexylbiphenyl and
p-[4-(2-ethylhexyl)-cyclohexyl]-p'-n-hexylbiphenyl.
p-(4-methylcyclohexyl)-p'-n-heptylbiphenyl,
p-(4-ethylcyclohexyl)-p'-n-heptylbiphenyl,
p-(4-n-propylcyclohexyl)-p'-n-heptylbiphenyl,
p-(4-n-butylcyclohexyl)-p'-n-heptylbiphenyl,
p-(4-n-pentylcycloheyxl)-p'-n-heptylbiphenyl,
p-(4-n-hexylcyclohexyl)-p'-n-heptylbiphenyl,
p-(4-n-heptylcyclohexyl)-p'-n-heptylbiphenyl,
p-(4-n-octylcyclohexyl)-p'-n-heptylbiphenyl,
p-(4-n-nonylcyclohexyl)-p'-n-heptylbiphenyl,
p-(4-n-decylcyclohexyl)-p'-n-heptylbiphenyl,
p-[4-(2-methylpropyl)-cyclohexyl]-p'-n-heptylbiphenyl,
p-[4-(2-methylbutyl)-cyclohexyl]-p'-n-heptylbiphenyl,
p-[4-(3-methylbutyl)-cyclohexyl]-p'-n-heptylbiphenyl and
p-[4-(2-ethylhexyl)-cyclohexyl]-p'-n-heptylbiphenyl.
p-(4-methylcyclohexyl)-p'-n-octylbiphenyl,
p-(4-ethylcyclohexyl)-p'-n-octylbiphenyl,
p-(4-n-propylcyclohexyl)-p'-n-octylbiphenyl,
p-(4-n-butylcyclohexyl)-p'-n-octylbiphenyl,
p-(4-n-pentylcyclohexyl)-p'-n-octylbiphenyl,
p-(4-n-hexylcyclohexyl)-p'-n-octylbiphenyl,
p-(4-n-heptylcyclohexyl)-p'-n-octylbiphenyl,
p-(4-n-octylcyclohexyl)-p'-n-octylbiphenyl,
p-[4-(2-methylpropyl)-cylohexyl]-p'-n-octylbiphenyl,
p-[4-(2-methylbutyl)-cyclohexyl]-p'-n-octylbiphenyl,
p-[4-(3-methylbutyl)-cyclohexyl]-p'-n-octylbiphenyl and
p-[4-(2-ethylhexyl)-cyclohexyl]-p'-n-octylbiphenyl.
p-(4-methylcyclohexyl)-p'-n-nonylbiphenyl,
p-(4-ethylcyclohexyl)-p'-n-nonylbiphenyl, p-(4-n-propylcyclohexyl)-p'-n-nonylbiphenyl,
p-(4-n-butylcyclohexyl)-p'-n-nonylbiphenyl,
p-(4-n-pentylcyclohexyl)-p'-n-nonylbiphenyl,
p-(4-n-hexylcyclohexyl)-p'-n-nonylbiphenyl,
p-(4-n-heptylcyclohexyl)-p'-n-nonylbiphenyl,
p-[4-(2-methylpropyl)-cyclohexyl]-p'-n-nonylbiphenyl,
p-[4-(2-methylbutyl)-cyclohexyl]-p'-n-nonylbiphenyl,
p-[4-(3-methylbutyl)-cyclohexyl]-p'-n-nonylbiphenyl and
p-[4-(2-ethylhexyl)-cyclohexyl]-p'-n-nonylbiphenyl.
p-(4-methylcyclohexyl)-p'-n-decylbiphenyl,
p-(4-ethylcyclohexyl)-p'-n-decylbiphenyl,
p-(4-n-propylcyclohexyl)-p'-n-decylbiphenyl,
p-(4-n-butylcyclohexyl)-p'-n-decylbiphenyl,
p-(4-n-pentylcyclohexyl)-p'-n-decylbiphenyl,
p-(4-n-hexylcyclohexyl)-p'-n-decylbiphenyl,
p-(4-n-heptylcyclohexyl)-p'-n-decylbiphenyl,
p-(4-n-octylcyclohexyl)-p'-n-decylbiphenyl,
p-[4-(2-methylpropyl)-cyclohexyl]-p'-n-decylbiphenyl,
p-[4-(2-methylbutyl)-cyclohexyl]-p'-n-decylbiphenyl,
p-[4-(3-methylbutyl)-cyclohexyl]-p'-n-decylbiphenyl and
p-[4-(2-ethylhexyl)-cyclohexyl]-p'-n-decylbiphenyl.
p-(4-methylcycohexyl)-p'-n-undecylbiphenyl,
p-(4-ethylcyclohexyl)-p'-n-undecylbiphenyl,
p-(4-n-propylcyclohexyl)-p'-n-undecylbiphenyl,
p-(4-n-butylcyclohexyl)-p'-n-undecylbiphenyl,
p-(4-n-pentylcyclohexyl)-p'-n-undecylbiphenyl,
p-(4-n-hexylcyclohexyl)-p'-n-undecylbiphenyl,
p-(4-n-heptylcyclohexyl)-p'-n-undecylbiphenyl,
p-(4-n-octylcyclohexyl)-p'-n-undecylbiphenyl,
p-[4-(2-methylpropyl)-cyclohexyl]-p'-n-undecylbiphenyl,
p-[4-(2-methylbutyl)-cyclohexyl]-p'-n-undecylbiphenyl,
p-[4-(3-methylbutyl)-cyclohexyl]-p'-n-undecylbiphenyl and
p-[4-(2-ethylhexyl)-cyclohexyl]-p'-n-undecylbiphenyl.
p-(4-methylcyclohexyl)-p'-n-dodecylbiphenyl,
p-(4-ethylcyclohexyl)-p'-n-dodecylbiphenyl,
p-(4-n-propylcyclohexyl)-p'-n-dodecylbiphenyl,
p-(4-n-butylcyclohexyl)-p'-n-dodecylbiphenyl,
p-(4-n-pentylcyclohexyl)-p'-n-dodecylbiphenyl,
p-(4-n-hexylcyclohexyl)-p'-n-dodecylbiphenyl,
p-(4-n-heptylcyclohexyl)-p'-n-dodecylbiphenyl,
p-(4-n-octylcyclohexyl)-p'-n-dodecylbiphenyl,
p-[4-(2-methylpropyl)-cyclohexyl]-p'-n-dodecylbiphenyl,
p-[4-(2-methylbutyl)-cyclohexyl]-p'-n-dodecylbiphenyl,
p-[4-(3-methylbutyl)-cyclohexyl]-p'-n-dodecylbiphenyl, and
p-[4-(2-ethylhexyl)-cyclohexyl]-p'-n-dodecylbiphenyl.
p-(4-methylcyclohexyl)-p'-(2-methylbutyl)-biphenyl,
p-(4-ethylcyclohexyl)-p'-(2-methylbutyl)-biphenyl,
p-(4-n-propylcyclohexyl)-p'-(2-methylbutyl)-biphenyl,
p-(4-n-butylcyclohexyl)-p'-(2-methylbutyl)-biphenyl,
p-(4-n-pentylcyclohexyl)-p'-(2-methylbutyl)-biphenyl, m. 50°, c. 88°;
p-(4-n-hexylcyclohexyl)-p'-(2-methylbutyl)-biphenyl,
p-(4-n-heptylcyclohexyl)-p'-(2-methylbutyl)-biphenyl,
p-(4-n-octylcyclohexyl)-p'-(2-methylbutyl)-biphenyl,
p-(4-n-nonylcyclohexyl)-p'-(2-methylbutyl)-biphenyl,
p-(4-n-decylcyclohexyl)-p'-(2-methylbutyl)-biphenyl,
p-(4-n-undecylcyclohexyl)-p'-(2-methylbutyl)-biphenyl and
p-(4-n-dodecylcyclohexyl)-p'-(2-methylbutyl)-biphenyl.
p-(4-methylcyclohexyl)-p'-(2-methylpentyl)-biphenyl,
p-(4-ethylcyclohexyl)-p'-(2-methylpentyl)-biphenyl,
p-(4-n-propylcyclohexyl)-p'-(2-methylpentyl)-biphenyl,
p-(4-n-butylcyclohexyl)-p'-(2-methylpentyl)-biphenyl,
p-(4-n-pentylcyclohexyl)-p'-(2-methylpentyl)-biphenyl,
p-(4-n-hexylcyclohexyl)-p'-(2-methylpentyl)-biphenyl,
p-(4-n-heptylcyclohexyl)-p'-(2-methylpentyl)-biphenyl,
p-(4-n-octylcyclohexyl)-p'-(2-methylpentyl)-biphenyl,
p-(4-n-nonylcyclohexyl)-p'-(2-methylpentyl)-biphenyl,
p-(4-n-decylcyclohexyl)-p'-(2-methylpentyl)-biphenyl,
p-(4-n-undecylcyclohexyl)-p'-(2-methylpentyl)-biphenyl and
p-(4-n-dodecylcyclohexyl)-p'-(2-methylpentyl)-biphenyl.
p-(4-methylcyclohexyl)-p'-(2-ethylhexyl)-biphenyl,
p-(4-ethylcyclohexyl)-p'-(2-ethylhexyl)-biphenyl,
p-(4-n-propylcyclohexyl)-p'-(2-ethylhexyl)-biphenyl,
p-(4-n-butylcyclohexyl)-p'-(2-ethylhexyl)-biphenyl,
p-(4-n-pentylcyclohexyl)-p'-(2-ethylhexyl)-biphenyl,
p-(4-n-hexylcyclohexyl)-p'-(2-ethylhexyl)-biphenyl,
p-(4n-heptylcyclohexyl)-p'-(2-ethylhexyl)-biphenyl,
p-(4-n-octylcyclohexyl)-p'-(2-ethylhexyl)-biphenyl,
p-(4-n-nonylcyclohexyl)-p'-(2-ethylhexyl)-biphenyl,
p-(4-n-decylcyclohexyl)-p'-(2-ethylhexyl)-biphenyl,
p-(4-n-undecylcyclohexyl)-p'-(2-ethylhexyl)-biphenyl and
p-(4-n-dodecylcyclohexyl)-p'-(2-ethylhexyl)-biphenyl.

EXAMPLE 2

A mixture of 20 ml of 33% hydrogen peroxide and 50 ml of 98% formic acid is added to a suspension of 35 g of p-(4-n-pentylcyclohexyl)-p'-acetylbiphenyl in 200 ml of 98% formic acid and the reaction mixture is stirred at room temperature for 72 hours. It is poured onto 1,000 g of ice and extracted twice with 500 ml of methylene chloride each time. The p-(4-n-pentylcyclohexyl)-p'-acetoxybiphenyl which remains after evaporating off the solvent is recrystallized from ethanol; m. 77°, c. 215°.

The following compounds are prepared analogously:
p-(4-methylcyclohexyl)-p'-acetoxybiphenyl,
p-(4-ethylcyclohexyl)-p'-acetoxybiphenyl,
p-(4-n-propylcyclohexyl)-p'-acetoxybiphenyl,
p-(4-n-butylcyclohexyl)-p'-acetoxybiphenyl,
p-(4-n-hexylcyclohexyl)-p'-acetoxybiphenyl,
p-(4-n-heptylcyclohexyl)-p'-acetoxybiphenyl,
p-(4-n-octylcyclohexyl)-p'-acetoxybiphenyl,
p-(4-n-nonylcyclohexyl)-p'-acetoxybiphenyl,
p-(4-n-decylcyclohexyl)-p'-acetoxybiphenyl,
p-(4-n-undecylcyclohexyl)-p'-acetoxybiphenyl,
p-(4-n-dodecylcyclohexyl)-p'-acetoxybiphenyl, p-[4-(2-methylpropyl)-cyclohexyl]-p'-acetoxybiphenyl,
p-[4-(2-methylbutyl)-cyclohexyl]-p'-acetoxybiphenyl,
p-[4-(3-methylbutyl)-cyclohexyl]-p'-acetoxybiphenyl and
p-[4-(2-ethylhexyl)-cyclohexyl]-p'-acetoxybiphenyl.

EXAMPLE 3

(a) 46 g of p-(4-n-pentylcyclohexyl)-p'-acetoxybiphenyl is suspended in 250 ml of water and 85 ml of ethanol with 20 g of sodium hydroxide. The suspension is heated to the boiling point under reflux for 2 hours and is then acidified with hydrochloric acid. The p-(4-n-pentylcyclohexyl)-p'-hydroxybiphenyl which has precipitated is filtered off and washed with water until neutral; m. 202°.

(b) A solution of 3.4 g of valeryl chloride in 20 ml of toluene is added dropwise to 9.0 g of p-(4-n-pentylcyclohexyl)-p'-hydroxybiphenyl over the course of 10 minutes at such a rate that the temperature does not exceed 30°. 2.5 g of pyridine is then added and the mixture is stirred at 20° for 12 hours. The reaction mixture is then poured into 500 ml of water and the organic phase is separated off, washed with water until neutral and evaporated. The p-(4-n-pentylcyclohexyl)-p'-n-pentanoyloxybiphenyl which remains is recrystallized from ethanol; m. 69°, c. 199°.

The following compounds are prepared analogously:
p-(4-methylcyclohexyl)-p'-propionyloxybiphenyl,
p-(4-ethylcyclohexyl)-p'-propionyloxybiphenyl,
p-(4-n-propylcyclohexyl)-p'-propionyloxybiphenyl,
p-(4-n-butylcyclohexyl)-p'-propionyloxybiphenyl,
p-(4-n-pentylcyclohexyl)-p'-propionyloxybiphenyl,
p-(4-n-hexylcyclohexyl)-p'-propionyloxybiphenyl,
p-(4-n-heptylcyclohexyl)-p'-propionyloxybiphenyl,
p-(4-n-octylcyclohexyl)-p'-propionyloxybiphenyl,
p-(4-n-nonylcyclohexyl)-p'-propionyloxybiphenyl,
p-(4-n-decylcyclohexyl)-p'-propionyloxybiphenyl,
p-(4-n-undecylcyclohexyl)-p'-propionyloxybiphenyl,
p-(4-n-dodecylcyclohexyl)-p'-propionyloxybiphenyl,
p-[4-(2-methylpropyl)-cyclohexyl]-p'-propionyloxybiphenyl,
p-[4-(2-methylbutyl)-cyclohexyl]-p'-propionyloxybiphenyl,
p-[4-(3-methylbutyl)-cyclohexyl]-p'-propionyloxybiphenyl and
p-[4-(2-ethylhexyl)-cyclohexyl]-p'-propionyloxybiphenyl.
p-(4-methylcyclohexyl)-p'-butyryloxybiphenyl,
p-(4-ethylcyclohexyl)-p'-butyryloxybiphenyl,
p-(4-n-propylcyclohexyl)-p'-butyryloxybiphenyl,
p-(4-n-butylcyclohexyl)-p'-butyryloxybiphenyl,
p-(4-n-pentylcyclohexyl)-p'-butyryloxybiphenyl,
p-(4-n-hexylcyclohexyl)-p'-butyryloxybiphenyl,
p-(4-n-heptylcyclohexyl)-p'-butyryloxybiphenyl,
p-(4-n-octylcyclohexyl)-p'-butyryloxybiphenyl,
p-(4-n-nonylcyclohexyl)-p'-butyryloxybiphenyl,
p-(4-n-decylcyclohexyl)-p'-butyryloxybiphenyl,
p-(4-n-undecylcyclohexyl)-p'-butyryloxybiphenyl,
p-(4-n-dodecylcyclohexyl)-p'-butyryloxybiphenyl,
p-[4-(2-methylpropyl)-cyclohexyl]-p'-butyryloxybiphenyl,
p-[4-(2-methylbutyl)-cyclohexyl]-p'-butyryloxybiphenyl,
p-[4-(3-methylbutyl)-cyclohexyl]-p'-butyryloxybiphenyl and
p-[4-(2-ethylhexyl)-cyclohexyl]-p'-butyryloxybiphenyl.
p-(4-methylcyclohexyl)-p'-n-pentanoyloxybiphenyl,
p-(4-ethylcyclohexyl)-p'-n-pentanoyloxybiphenyl,
p-(4-n-propylcyclohexyl)-p'-n-pentanoyloxybiphenyl,
p-(4-n-butylcyclohexyl)-p'-n-pentanoyloxybiphenyl,
p-(4-n-hexylcyclohexyl)-p'-n-pentanoyloxybiphenyl,
p-(4-n-heptylcyclohexyl)-p'-n-pentanoyloxybiphenyl
p-(4-n-octylcyclohexyl)-p'-n-pentanoyloxybiphenyl,
p-(4-n-nonylcyclohexyl)-p'-n-pentanoyloxybiphenyl,
p-(4-n-decylcyclohexyl)-p'-n-pentanoyloxybiphenyl,
p-(4-n-undecylcyclohexyl)-p'-n-pentanoyloxybiphenyl,
p-(4-n-dodecylcyclohexyl)-p'-n-pentanoyloxybiphenyl,
p-[4-(2-methylpropyl)-cyclohexyl]-p'-pentanoyloxybiphenyl,
p-[4-(2-methylbutyl)-cyclohexyl]-p'-n-pentanoyloxybiphenyl,
p-[4-(3-methylbutyl)-cyclohexyl]-p'-n-pentanoyloxybiphenyl and
p-[4-(2-ethylhexyl)-cyclohexyl]-p'-n-pentanoyloxybiphenyl.
p-(4-methylcyclohexyl)-p'-n-hexanoyloxybiphenyl,
p-(4-ethylcyclohexyl)-p'-n-hexanoyloxybiphenyl,
p-(4-n-propylcyclohexyl)-p'-n-hexanoyloxybiphenyl,
p-(4-n-butylcyclohexyl)-p'-n-hexanoyloxybiphenyl,
p-(4-n-pentylcyclohexyl)-p'-hexanoyloxybiphenyl,
p-(4-n-hexylcyclohexyl)-p'-n-hexanoyloxybiphenyl,
p-(4-n-heptylcyclohexyl)-p'-n-hexanoyloxybiphenyl,
p-(4-n-octylcyclohexyl)-p'-n-hexanoyloxybiphenyl,
p-(4-n-nonylcyclohexyl)-p'-n-hexanoyloxybiphenyl,
p-(4-n-decylcyclohexyl)-p'-n-hexanoyloxybiphenyl,
p-(4-n-undecylcyclohexyl)-p'-n-hexanoyloxybiphenyl,
p-(4-n-dodecylcyclohexyl)-p'-n-hexanoyloxybiphenyl,
p-[4-(2-methylpropyl)-cyclohexyl]-p'-n-hexanoyloxybiphenyl,
p-[4-(2-methylbutyl)-cyclohexyl]-p'-n-hexanoyloxybiphenyl,
p-[4-(3-methylbutyl)-cyclohexyl]-p'-n-hexanoyloxybiphenyl and
p-[4-(2-ethylhexyl)-cyclohexyl]-p'-n-hexanoyloxybiphenyl.
p-(4-methylcyclohexyl)-p'-n-heptanoyloxybiphenyl,
p-(4-ethylcyclohexyl)-p'-n-heptanoyloxybiphenyl,
p-(4-n-propylcyclohexyl)-p'-n-heptanoyloxybiphenyl,
p-(4-n-butylcyclohexyl)-p'-n-heptanoyloxybiphenyl,
p-(4-n-pentylcyclohexyl)-p'-n-heptanoyloxybiphenyl,
p-(4-n-hexylcyclohexyl)-p'-n-heptanoyloxybiphenyl,
p-(4-n-heptylcyclohexyl)-p'-n-heptanoyloxybiphenyl,
p-(4-n-octylcyclohexyl)-p'-n-heptanoyloxybiphenyl,
p-(4-n-nonylcyclohexyl)-p'-n-heptanoyloxybiphenyl,
p-(4-n-decylcyclohexyl)-p'-n-heptanoyloxybiphenyl,
p-[4-(2-methylpropyl)-cyclohexyl]-p'-n-heptanoyloxybiphenyl,
p-[4-(2-methylbutyl)-cyclohexyl]-p'-n-heptanoyloxybiphenyl,
p-[4-(3-methylbutyl)-cyclohexyl]-p'-n-heptanoyloxybiphenyl and
p-[4-(2-ethylhexyl)-cyclohexyl]-p'-n-heptanoyloxybiphenyl.
p-(4-methylcyclohexyl)-p'-n-octanoyloxybiphenyl,
p-(4-ethylcyclohexyl)-p'-n-octanoyloxybiphenyl,
p-(4-n-propylcyclohexyl)-p'-n-octanoyloxybiphenyl, p-(4-n-butylcyclohexyl)-p'-n-octanoyloxybiphenyl,
p-(4-n-pentylcyclohexyl)-p'-n-octanoyloxybiphenyl,
p-(4-n-hexylcyclohexyl)-p'-n-octanoyloxybiphenyl,
p-(4-n-heptylcyclohexyl)-p'-n-octanoyloxybiphenyl,
p-(4-n-octylcyclohexyl)-p'-n-octanoyloxybiphenyl,
p-[4-(2-methylpropyl)-cyclohexyl]-p'-n-octanoyloxybiphenyl,
p-[4-(2-methylbutyl)-cyclohexyl]-p'-n-octanoyloxybiphenyl,
p-[4-(3-methylbutyl)-cyclohexyl]-p'-n-octanoyloxybiphenyl and
p-[4-(2-ethylhexyl)-cyclohexyl]-p'-n-octanoyloxybiphenyl.
p-(4-methylcyclohexyl)-p'-trifluoroacetoxybiphenyl,
p-(4-ethylcyclohexyl)-p'-trifluoroacetoxybiphenyl,
p-(4-n-propylcyclohexyl)-p'-trifluoroacetoxybiphenyl,
p-(4-n-butylcyclohexyl)-p'-trifluoroacetoxybiphenyl,
p-(4-n-pentylcyclohexyl)-p'-trifluoroacetoxybiphenyl,
p-(4-n-hexylcyclohexyl)-p'-trifluoroacetoxybiphenyl,
p-(4-n-heptylcyclohexyl)-p'-trifluoroacetoxybiphenyl,
p-(4-n-octylcyclohexyl)-p'-trifluoroacetoxybiphenyl,
p-(4-n-nonylcyclohexyl)-p'-trifluoroacetoxybiphenyl,
p-(4-n-decylcyclohexyl)-p'-trifluoroacetoxybiphenyl,
p-(4-n-undecylcyclohexyl)-p'-trifluoroacetoxybiphenyl,
p-(4-n-dodecylcyclohexyl)-p'-trifluoroacetoxybiphenyl,
p-[4-(2-methylpropyl)-cyclohexyl]-p'-trifluoroacetoxybiphenyl,
p-[4-(2-methylbutyl)-cyclohexyl]-p'-trifluoroacetoxybiphenyl,
p-[4-(3-methylbutyl)-cyclohexyl]-p'-trifluoroacetoxybiphenyl and
p-[4-(2-ethylhexyl)-cyclohexyl]-p'-trifluoroacetoxybiphenyl.
p-(4-methylcyclohexyl)-p'-heptafluorobutyryloxybiphenyl,
p-(4-ethylcyclohexyl)-p'-heptafluorobutyryloxybiphenyl,
p-(4-n-propylcyclohexyl)-p'-heptafluorobutyryloxybiphenyl,
p-(4-n-butylcyclohexyl)-p'-heptafluorobutyryloxybiphenyl,
p-(4-n-pentylcyclohexyl)-p'-heptafluorobutyryloxybiphenyl,
p-(4-n-hexylcyclohexyl)-p'-heptafluorobutyryloxybiphenyl,
p-(4-n-heptylcyclohexyl)-p'-heptafluorobutyryloxybiphenyl,
p-(4-n-octylcyclohexyl)-p'-heptafluorobutyryloxybiphenyl,
p-(4-n-nonylcyclohexyl)-p'-heptafluorobutyryloxybiphenyl,
p-(4-n-decylcyclohexyl)-p'-heptafluorobutyryloxybiphenyl,
p-[4-(2-methylpropyl)-cyclohexyl]-p'-heptafluorobutyryloxybiphenyl,
p-[4-(2-methylbutyl)-cyclohexyl]-p'-heptafluorobutyryloxybiphenyl,
p-[4-(3-methylbutyl)-cyclohexyl]-p'-heptafluorobutyryloxybiphenyl and
p-[4-(2-ethylhexyl)-cyclohexyl]-p'-heptafluorobutyryloxybiphenyl.

EXAMPLE 4

A solution of 32 g of p-(4-pentylcyclohexyl)-p'-hydroxybiphenyl in 250 ml of acetone is heated to the boiling point under reflux with 31 g of n-pentyl bromide in the presence of 70 g of anhydrous potassium carbonate for 24 hours. After cooling, the reaction mixture is filtered, the filtrate is evaporated and the p-(4-n-pentylcyclohexyl)-p'-n-pentyloxybiphenyl which remains is recrystallized from ethanol; m. 42°, c. 183°, yield: 37 g.

The following compounds are prepared analogously:
p-(4-methylcyclohexyl)-p'-methoxy-biphenyl,
p-(4-ethylcyclohexyl)-p'-methoxy-biphenyl,
p-(4-n-propylcyclohexyl)-p'-methoxy-biphenyl,
p-(4-n-butylcyclohexyl)-p'-methoxy-biphenyl,
p-(4-n-pentylcyclohexyl)-p'-methoxy-biphenyl, m. 80°, c. 165°;
p-(4-n-hexylcyclohexyl)-p'-methoxy-biphenyl,
p-(4-n-heptylcyclohexyl)-p'-methoxy-biphenyl,
p-(4-n-octylcyclohexyl)-p'-methoxy-biphenyl,
p-(4-n-nonylcyclohexyl)-p'-methoxy-biphenyl,
p-(4-n-decylcyclohexyl)-p'-methoxy-biphenyl,
p-(4-n-undecylcyclohexyl)-p'-methoxy-biphenyl,
p-(4-n-dodecylcyclohexyl)-p'-methoxy-biphenyl,
p-[4-(2-methylpropyl)-cyclohexyl]-p'-methoxy-biphenyl,
p-[4-(2-methylbutyl)-cyclohexyl]-p'-methoxy-biphenyl,
p-[4-(3-methylbutyl)-cyclohexyl]-p'-methoxy-biphenyl and
p-[4-(2-ethylhexyl)-cyclohexyl]-p'-methoxy-biphenyl.
p-(4-methylcyclohexyl)-p'-ethoxy-biphenyl,
p-(4-ethylcyclohexyl)-p'-ethoxy-biphenyl,
p-(4-n-propylcyclohexyl)-p'-ethoxy-biphenyl,
p-(4-n-butylcyclohexyl)-p'-ethoxy-biphenyl,
p-(4-n-pentylcyclohexyl)-p'-ethoxy-biphenyl, m. 89°, c. 148°;
p-(4-n-hexylcyclohexyl)-p'-ethoxy-biphenyl,
p-(4-n-heptylcyclohexyl)-p'-ethoxy-biphenyl,
p-(4-n-octylcyclohexyl)-p'-ethoxy-biphenyl,
p-(4-n-nonylcyclohexyl)-p'-ethoxy-biphenyl,
p-(4-n-decylcyclohexyl)-p'-ethoxy-biphenyl,
p-(4-n-undecylcyclohexyl)-p'-ethoxy-biphenyl,
p-(4-n-dodecylcyclohexyl)-p'-ethoxy-biphenyl,
p-[4-(2-methylpropyl)-cyclohexyl]-p'-ethoxy-biphenyl,
p-[4-(2-methylbutyl)-cyclohexyl]-p'-ethoxy-biphenyl,
p-[4-(3-methylbutyl)-cyclohexyl]-p'-ethoxy-biphenyl and
p-[4-(2-ethylhexyl)-cyclohexyl]-p'-ethoxy-biphenyl.
p-(4-methylcyclohexyl)-p'-n-propyloxybiphenyl,
p-(4-ethylcyclohexyl)-p'-n-propyloxybiphenyl,
p-(4-n-propylcyclohexyl)-p'-n-propyloxybiphenyl,
p-(4-n-butylcyclohexyl)-p'-n-propyloxybiphenyl,
p-(4-n-pentylcyclohexyl)-p'-n-propyloxybiphenyl,
p-(4-n-hexylcyclohexyl)-p'-n-propyloxybiphenyl,
p-(4-n-heptylcyclohexyl)-p'-n-propyloxybiphenyl,
p-(4-n-octylcyclohexyl)-p'-n-propyloxybiphenyl,
p-(4-n-nonylcyclohexyl)-p'-n-propyloxybiphenyl,
p-(4-n-decylcyclohexyl)-p'-n-propyloxybiphenyl,
p-(4-n-undecylcyclohexyl)-p'-n-propyloxybiphenyl,
p-(4-n-dodecylcyclohexyl)-p'-n-propyloxybiphenyl,
p-[4-(2-methylpropyl)-cyclohexyl]-p'-n-propyloxybiphenyl,
p-[4-(2-methylbutyl)-cyclohexyl]-p'-n-propyloxybiphenyl, p-[4-(3-methylbutyl)-cyclohexyl]-p'-n-propyloxybiphenyl and
p-[4-(2-ethylhexyl)-cyclohexyl]-p'-n-propyloxybiphenyl.
p-(4-methylcyclohexyl)-p'-n-butyloxybiphenyl,
p-(4-ethylcyclohexyl)-p'-n-butyloxybiphenyl,
p-(4-n-propylcyclohexyl)-p'-n-butyloxybiphenyl,
p-(4-n-butylcyclohexyl)-p'-n-butyloxybiphenyl,
p-(4-n-pentylcyclohexyl)-p'-n-butyloxybiphenyl,
p-(4-n-hexylcyclohexyl)-p'-n-butyloxybiphenyl,
p-(4-n-heptylcyclohexyl)-p'-n-butyloxybiphenyl,
p-(4-n-octylcyclohexyl)-p'-n-butyloxybiphenyl,
p-(4-n-nonylcyclohexyl)-p'-n-butyloxybiphenyl,
p-(4-n-decylcyclohexyl)-p'-n-butyloxybiphenyl,
p-[4-(2-methylpropyl)-cyclohexyl]-p'-n-butyloxybiphenyl,
p-[4-(2-methylbutyl)-cyclohexyl]-p'-n-butyloxybiphenyl,
p-[4-(3-methylbutyl)-cyclohexyl]-p'-n-butyloxybiphenyl and
p-[4-(2-ethylhexyl)-cyclohexyl]-p'-n-butyloxybiphenyl.
p-(4-methylcyclohexyl)-p'-n-pentyloxybiphenyl,
p-(4-ethylcyclohexyl)-p'-n-pentyloxybiphenyl,
p-(4-n-propylcyclohexyl)-p'-n-pentyloxybiphenyl,
p-(4-n-butylcyclohexyl)-p'-n-pentyloxybiphenyl,
p-(4-n-hexylcyclohexyl)-p'-n-pentyloxybiphenyl,
p-(4-n-heptylcyclohexyl)-p'-n-pentyloxybiphenyl,
p-(4-n-octylcyclohexyl)-p'-n-pentyloxybiphenyl,
p-(4-n-nonylcyclohexyl)-p'-n-pentyloxybiphenyl,
p-(4-n-decylcyclohexyl)-p'-n-pentyloxybiphenyl,
p-(4-n-undecylcyclohexyl)-p'-n-pentyloxybiphenyl,
p-(4-n-dodecylcyclohexyl)-p'-n-pentyloxybiphenyl,
p-[4-(2-methylpropyl)-cyclohexyl]-p'-n-pentyloxybiphenyl,
p-[4-(2-methylbutyl)-cyclohexyl]-p'-n-pentyloxybiphenyl,
p-[4-(3-methylbutyl)-cyclohexyl]-p'-n-pentyloxybiphenyl and
p-[4-(2-ethylhexyl)-cyclohexyl]-p'-n-pentyloxybiphenyl.
p-(4-methylcyclohexyl)-p'-n-hexyloxybiphenyl,
p-(4-ethylcyclohexyl)-p'-n-hexyloxybiphenyl,
p-(4-n-propylcyclohexyl)-p'-n-hexyloxybiphenyl,
p-(4-n-butylcyclohexyl)-p'-n-hexyloxybiphenyl,
p-(4-n-pentylcyclohexyl)-p'-n-hexyloxybiphenyl,
p-(4-n-hexylcyclohexyl)-p'-n-hexyloxybiphenyl,
p-(4-n-heptylcyclohexyl)-p'-n-hexyloxybiphenyl,
p-(4-n-octylcyclohexyl)-p'-n-hexyloxybiphenyl,
p-(4-n-nonylcyclohexyl)-p'-n-hexyloxybiphenyl,
p-(4-n-decylcyclohexyl)-p'-n-hexyloxybiphenyl,
p-[4-(2-methylpropyl)-cyclohexyl]-p'-hexyloxybiphenyl,
p-[4-(2-methylbutyl)-cyclohexyl]-p'-n-hexyloxybiphenyl,
p-[4-(3-methylbutyl)-cyclohexyl]-p'-n-hexyloxybiphenyl and
p-[4-(2-ethylhexyl)-cyclohexyl]-p'-n-hexyloxybiphenyl.
p-(4-methylcyclohexyl)-p'-n-heptyloxybiphenyl,
p-(4-ethylcyclohexyl)-p'-n-heptyloxybiphenyl,
p-(4-n-propylcyclohexyl)-p'-n-heptyloxybiphenyl,
p-(4-n-butylcyclohexyl)-p'-n-heptyloxybiphenyl,
p-(4-n-pentylcyclohexyl)-p'-n-heptyloxybiphenyl,
p-(4-n-hexylcyclohexyl)-p'-n-heptyloxybiphenyl,
p-(4-n-heptylcyclohexyl)-p'-n-heptyloxybiphenyl,
p-(4-n-octylcyclohexyl)-p'-n-heptyloxybiphenyl,
p-(4-n-nonylcyclohexyl)-p'-n-heptyloxybiphenyl,
p-(4-n-decylcyclohexyl)-p'-n-heptyloxybiphenyl,
p-[4-(2-methylpropyl)-cyclohexyl]-p'-n-heptyloxybiphenyl,
p-[4-(2-methylbutyl)-cyclohexyl]-p'-n-heptyloxybiphenyl,
p-[4-(3-methylbutyl)-cyclohexyl]-p'-n-heptyloxybiphenyl and
p-[4-(2-ethylhexyl)-cyclohexyl]-p'-n-heptyloxybiphenyl.
p-(4-methylcyclohexyl)-p'-n-octyloxybiphenyl,
p-(4-ethylcyclohexyl)-p'-n-octyloxybiphenyl,
p-(4-n-propylcyclohexyl)-p'-n-octyloxybiphenyl,
p-(4-n-butylcyclohexyl)-p'-n-octyloxybiphenyl,
p-(4-n-pentylcyclohexyl)-p'-n-octyloxybiphenyl,
p-(4-n-hexylcyclohexyl)-p'-n-octyloxybiphenyl,
p-(4-n-heptylcyclohexyl)-p'-n-octyloxybiphenyl,
p-(4-n-octylcyclohexyl)-p'-n-octyloxybiphenyl,
p-[4-(2-methylpropyl)-cyclohexyl]-p'-n-octyloxybiphenyl,
p-[4-(2-methylbutyl)-cyclohexyl]-p'-n-octyloxybiphenyl,
p-[4-(3-methylbutyl)-cyclohexyl]-p'-n-octyloxybiphenyl and
p-[4-(2-ethylhexyl)-cyclohexyl]-p'-n-octyloxybiphenyl.
p-(4-methylcyclohexyl)-p'-n-nonyloxybiphenyl,
p-(4-ethylcyclohexyl)-p'-n-nonyloxybiphenyl,
p-(4-n-propylcyclohexyl)-p'-n-nonyloxybiphenyl,
p-(4-n-butylcyclohexyl)-p'-n-nonyloxybiphenyl,
p-(4-n-pentylcyclohexyl)-p'-n-nonyloxybiphenyl,
p-(4-n-hexylcyclohexyl)-p'-n-nonyloxybiphenyl,
p-(4-n-heptylcyclohexyl)-p'-n-nonyloxybiphenyl,
p-(4-n-octylcyclohexyl)-p'-n-nonyloxybiphenyl,
p-[4-(2-methylpropyl)-cyclohexyl]-p'-n-nonyloxybiphenyl,
p-[4-(2-methylbutyl)-cyclohexyl]-p'-n-nonyloxybiphenyl and
p-[4-(3-methylbutyl)-cyclohexyl]-p'-n-nonyloxybiphenyl.
p-(4-methylcyclohexyl)-p'-n-decyloxybiphenyl,
p-(4-ethycyclohexyl)-p'-n-decyloxybiphenyl,
p-(4-n-propylcyclohexyl)-p'-n-decyloxybiphenyl,
p-(4-n-butylcyclohexyl)-p'-n-decyloxybiphenyl,
p-(4-n-pentylcyclohexyl)-p'-n-decyloxybiphenyl,
p-(4-n-hexylcyclohexyl)-p'-n-decyloxybiphenyl,
p-(4-n-heptylcyclohexyl)-p'-n-decyloxybiphenyl,
p-(4-n-octylcyclohexyl)-p'-n-decyloxybiphenyl,
p-[4-(2-methylpropyl)-cyclohexyl]-p'-n-decyloxybiphenyl,
p-[4-(2-methylbutyl)-cyclohexyl]-p'-n-decyloxybiphenyl and
p-[4-(3-methylbutyl)-cyclohexyl]-p'-n-decyloxybiphenyl.
p-(4-methycyclohexyl)-p'-n-undecyloxybiphenyl,
p-(4-ethylcyclohexyl)-p'-n-undecyloxybiphenyl,
p-(4-n-propylcyclohexyl)-p'-n-undecyloxybiphenyl,
p-(4-n-butylcyclohexyl)-p'-n-undecyloxybiphenyl,
p-(4-n-pentylcyclohexyl)-p'-n-undecyloxybiphenyl,
p-(4-n-hexylcyclohexyl)-p'-n-undecyloxybiphenyl,
p-(4-n-heptylcyclohexyl)-p'-n-undecyloxybiphenyl,
p-[4-(2-methylpropyl)-cyclohexyl]-p'-n-undecyloxybiphenyl,
p-[4-(2-methylbutyl)-cyclohexyl]-p'-n-undecyloxybiphenyl and
p-[4-(3-methylbutyl)-cyclohexyl]-p'-n-undecyloxybiphenyl.
p-(4-methylcyclohexyl)-p'-n-dodecyloxybiphenyl,
p-(4-ethylcyclohexyl)-p'-n-dodecyloxybiphenyl, p-(4-n-propylcyclohexyl)-p'-n-dodecyloxybiphenyl,
p-(4-n-butylcyclohexyl)-p'-n-dodecyloxybiphenyl,
p-(4-n-pentylcyclohexyl)-p'-n-dodecyloxybiphenyl,
p-(4-n-hexylcyclohexyl)-p'-n-dodecyloxybiphenyl,
p-(4-n-heptylcyclohexyl)-p'-n-dodecyloxybiphenyl,
p-[4-(2-methylpropyl)-cyclohexyl]-p'-n-dodecyloxybiphenyl and
p-[4-(2-methylbutyl)-cyclohexyl]-p'-n-dodecyloxybiphenyl.
p-(4-methylcyclohexyl)-p'-(2-methylbutyloxy)-biphenyl,
p-(4-ethylcyclohexyl)-p'-(2-methylbutyloxy)-biphenyl,
p-(4-n-propylcyclohexyl)-p'-(2-methylbutyloxy)-biphenyl,
p-(4-n-butylcyclohexyl)-p'-(2-methylbutyloxy)-biphenyl,
p-(4-n-pentylcyclohexyl)-p'-(2-methylbutyloxy)-biphenyl,
p-(4-n-hexylcyclohexyl)-p'-(2-methylbutyloxy)-biphenyl,
p-(4-n-heptylcyclohexyl)-p'-(2-methylbutyloxy)-biphenyl,
p-(4-n-octylcyclohexyl)-p'-(2-methylbutyloxy)-biphenyl,
p-(4-n-nonylcyclohexyl)-p'-(2-methylbutyloxy)-biphenyl,
p-(4-n-decylcyclohexyl)-p'-(2-methylbutyloxy)-biphenyl,
p-(4-n-undecylcyclohexyl)-p'-(2-methylbutyloxy)-biphenyl and
p-(4-n-dodecylcyclohexyl)-p'-(2-methylbutyloxy)-biphenyl,
p-(4-methylcyclohexyl)-p'-(2-methylheptyloxy)-biphenyl,
p-(4-ethylcyclohexyl)-p'-(2-methylheptyloxy)-biphenyl,
p-(4-n-propylcyclohexyl)-p'-(2-methylheptyloxy)-biphenyl,
p-(4-n-butylcyclohexyl)-p'-(2-methylheptyloxy)-biphenyl,
p-(4-n-pentylcyclohexyl)-p'-(2-methylheptyloxy)-biphenyl,
p-(4-n-hexylcyclohexyl)-p'-(2-methylheptyloxy)-biphenyl,
p-(4-n-heptylcyclohexyl)-p'-(2-methylheptyloxy)-biphenyl,
p-(4-n-octylcyclohexyl)-p'-(2-methylheptyloxy)-biphenyl,
p-(4-n-nonylcyclohexyl)-p'-(2-methylheptyloxy)-biphenyl and
p-(4-n-decylcyclohexyl)-p'-(2-methylheptyloxy)-biphenyl.

EXAMPLE 5

A solution of 32 g of p-(4-n-pentylcyclohexyl)-p'-hydroxybiphenyl in 200 ml of toluene is heated to the boiling point under reflux with 42 g of heptafluorobutyric anhydride and 2 drops of concentrated sulfuric acid for 7 hours. The cooled reaction mixture is washed with 150 ml of aqueous sodium bicarbonate solution, dried over sodium sulfate and evaporated. The p-(4-n-pentylcyclohexyl)-p'-heptafluorobutyryloxybiphenyl which remains is heated at 170° in a pressure vessel in the presence of 25 g of anhydrous hydrofluoric acid and 108 g of sulfur tetrafluoride for 8 hours. The volatile constituents of the reaction mixture are then removed by bubbling out with nitrogen, the residue is taken up in a suspension of 50 g of sodium fluoride in 250 ml of tetrahydrofuran and, after stirring for 2 hours, the resulting suspension is filtered. The filtrate is evaporated and the p-(4-n-pentylcyclohexyl)-p'-perfluorobutyloxybiphenyl which remains is recrystallized from ethanol.

The following compounds are prepared analogously:
p-(4-methylcyclohexyl)-p'-perfluoroethoxybiphenyl,
p-(4-ethylcyclohexyl)-p'-perfluoroethoxybiphenyl,
p-(4-n-propylcyclohexyl)-p'-perfluoroethoxybiphenyl,
p-(4-n-butylcyclohexyl)-p'-perfluoroethoxybiphenyl,
p-(4-n-pentylcyclohexyl)-p'-perfluoroethoxybiphenyl,
p-(4-n-hexylcyclohexyl)-p'-perfluoroethoxybiphenyl,
p-(4-n-heptylcyclohexyl)-p'-perfluoroethoxybiphenyl,
p-(4-n-octylcyclohexyl)-p'-perfluoroethoxybiphenyl,
p-(4-n-nonylcyclohexyl)-p'-perfluoroethoxybiphenyl and
p-(4-n-decylcyclohexyl)-p'-perfluoroethoxybiphenyl.
p-(4-methylcyclohexyl)-p'-perfluoropropyloxybiphenyl,
p-(4-ethylcyclohexyl)-p'-perfluoropropyloxybiphenyl,
p-(4-n-propylcyclohexyl)-p'-perfluoropropyloxybiphenyl,
p-(4-n-butylcyclohexyl)-p'-perfluoropropyloxybiphenyl,
p-(4-n-pentylcyclohexyl)-p'-perfluoropropyloxybiphenyl,
p-(4-n-hexylcyclohexyl)-p'-perfluoropropyloxybiphenyl,
p-(4-n-heptylcyclohexyl)-p'-perfluoropropyloxybiphenyl,
p-(4-n-octylcyclohexyl)-p'-perfluoropropyloxybiphenyl,
p-(4-n-nonylcyclohexyl)-p'-perfluoropropyloxybiphenyl and
p-(4-n-decylcyclohexyl)-p'-perfluoropropyloxybiphenyl.
p-(4-methylcyclohexyl)-p'-perfluorobutyloxybiphenyl,
p-(4-ethylcyclohexyl)-p'-perfluorobutyloxybiphenyl,
p-(4-n-propylcyclohexyl)-p'-perfluorobutyloxybiphenyl,
p-(4-n-butylcyclohexyl)-p'-perfluorobutyloxybiphenyl,
p-(4-n-hexylcyclohexyl)-p'-perfluorobutyloxybiphenyl,
p-(4-n-heptylcyclohexyl)-p'-perfluorobutyloxybiphenyl,
p-(4-n-octylcyclohexyl)-p'-perfluorobutyloxybiphenyl,
p-(4-n-nonylcyclohexyl)-p'-perfluorobutyloxybiphenyl and
p-(4-n-decylcyclohexyl)-p'-perfluorobutyloxybiphenyl.
p-(4-methylcyclohexyl)-p'-perfluoropentyloxybiphenyl,
p-(4-ethylcyclohexyl)-p'-perfluoropentyloxybiphenyl,
p-(4-n-propylcyclohexyl)-p'-perfluoropentyloxybiphenyl,
p-(4-n-butylcyclohexyl)-p'-perfluoropentyloxybiphenyl, p-(4-n-pentylcyclohexyl)-p'-perfluoropentyloxybiphenyl,
p-(4-n-hexylcyclohexyl)-p'-perfluoropentyloxybiphenyl,
p-(4-n-heptylcyclohexyl)-p'-perfluoropentyloxybiphenyl and
p-(4-n-octylcyclohexyl)-p'-perfluoropentyloxybiphenyl.

EXAMPLE 6 p-(4-n-Pentylcyclohexyl)-p'-trifluoroacetylbiphenyl is prepared from 4-(4-n-pentylcyclohexyl)-biphenyl and trifluoroacetyl chloride in the presence of aluminum chloride, analogously to Example 1(a). 40 g of the compound obtained is heated at 100° in a pressure vessel with 50 g of sulfur tetrafluoride for 8 hours. After cooling, the excess sulfur tetrafluoride and volatile reaction products are removed by bubbling nitrogen in, and the p-(4-n-pentylcyclohexyl)-p'-perfluoroethylbiphenyl which remains is recrystallized from ethanol.

The following compounds are prepared analogously:
p-(4-methylcyclohexyl)-p'-trifluoromethylbiphenyl,
p-(4-ethylcyclohexyl)-p'-trifluoromethylbiphenyl,
p-(4-n-propylcyclohexyl)-p'-trifluoromethylbiphenyl,
p-(4-n-butylcyclohexyl)-p'-trifluoromethylbiphenyl,
p-(4-n-pentylcyclohexyl)-p'-trifluoromethylbiphenyl,
p-(4-n-hexylcyclohexyl)-p'-trifluoromethylbiphenyl,
p-(4-n-heptylcyclohexyl)-p'-trifluoromethylbiphenyl,
p-(4-n-octylcyclohexyl)-p'-trifluoromethylbiphenyl,
p-(4-n-nonylcyclohexyl)-p'-trifluoromethylbiphenyl and
p-(4-n-decylcyclohexyl)-p'-trifluoromethylbiphenyl.
p-(4-methylcyclohexyl)-p'-perfluoroethylbiphenyl,
p-(4-ethylcyclohexyl)-p'-perfluoroethylbiphenyl,
p-(4-n-propylcyclohexyl)-p'-perfluoroethylbiphenyl,
p-(4-n-butylcyclohexyl)-p'-perfluoroethylbiphenyl,
p-(4-n-hexylcyclohexyl)-p'-perfluoroethylbiphenyl,
p-(4-n-heptylcyclohexyl)-p'-perfluoroethylbiphenyl,
p-(4-n-octylcyclohexyl)-p'-perfluoroethylbiphenyl,
p-(4-n-nonylcyclohexyl)-p'-perfluoroethylbiphenyl,
p-(4-n-decylcyclohexyl)-p'-perfluoroethylbiphenyl,
p-[4-(2-methylpropyl)-cyclohexyl]-p'-perfluoroethylbiphenyl,
p-[4-(2-methylbutyl)-cyclohexyl]-p'-perfluoroethylbiphenyl,
p-[4-(3-methylbutyl)-cyclohexyl]-p'-perfluoroethylbiphenyl and
p-[4-(2-ethylhexyl)-cyclohexyl]-p'-perfluoroethylbiphenyl.
p-(4-methylcyclohexyl)-p'-perfluoropropylbiphenyl,
p-(4-ethylcyclohexyl)-p'-perfluoropropylbiphenyl,
p-(4-n-propylcyclohexyl)-p'-perfluoropropylbiphenyl,
p-(4-n-butylcyclohexyl)-p'-perfluoropropylbiphenyl,
p-(4-n-pentylcyclohexyl)-p'-perfluoropropylbiphenyl,
p-(4-n-hexylcyclohexyl)-p'-perfluoropropylbiphenyl,
p-(4-n-heptylcyclohexyl)-p'-perfluoropropylbiphenyl,
p-(4-n-octylcyclohexyl)-p'-perfluoropropylbiphenyl,
p-(4-n-nonylcyclohexyl)-p'-perfluoropropylbiphenyl and
p-(4-n-decylcyclohexyl)-p'-perfluoropropylbiphenyl.
p-(4-methylcyclohexyl)-p'-perfluorobutylbiphenyl,
p-(4-ethylcyclohexyl)-p'-perfluorobutylbiphenyl,
p-(4-n-propylcyclohexyl)-p'-perfluorobutylbiphenyl,
p-(4-n-butylcyclohexyl)-p'-perfluorobutylbiphenyl,
p-(4-n-pentylcyclohexyl)-p'-perfluorobutylbiphenyl,
p-(4-n-hexylcyclohexyl)-p'-perfluorobutylbiphenyl,
p-(4-n-heptylcyclohexyl)-p'-perfluorobutylbiphenyl and
p-(4-n-octylcyclohexyl)-p'-perfluorobutylbiphenyl.
p-(4-methylcyclohexyl)-p'-perfluoropentylbiphenyl,
p-(4-ethylcyclohexyl)-p'-perfluoropentylbiphenyl,
p-(4-n-propylcyclohexyl)-p'-perfluoropentylbiphenyl,
p-(4-n-butylcyclohexyl)-p'-perfluoropentylbiphenyl,
p-(4-n-pentylcyclohexyl)-p'-perfluoropentylbiphenyl,
p-(4-n-hexylcyclohexyl)-p'-perfluoropentylbiphenyl
p-(4-n-heptylcyclohexyl)-p'-perfluoropentylbiphenyl and
p-(4-n-octylcyclohexyl)-p'-perfluoropentylbiphenyl.
p-(4-methylcyclohexyl)-p'-perfluoroisobutylbiphenyl,
p-(4-ethylcyclohexyl)-p'-perfluoroisobutylbiphenyl,
p-(4-n-propylcyclohexyl)-p'-perfluoroisobutylbiphenyl,
p-(4-n-butylcyclohexyl)-p'-perfluoroisobutylbiphenyl,
p-(4-n-pentylcyclohexyl)-p'-perfluoroisobutylbiphenyl,
p-(4-n-hexylcyclohexyl)-p'-perfluoroisobutylbiphenyl
p-(4-n-heptylcyclohexyl)-p'-perfluoroisobutylbiphenyl and
p-(4-n-octylcyclohexyl)-p'-perfluoroisobutylbiphenyl.

The following examples relate to dielectrics of this invention.

EXAMPLE 7

A dielectric consisting of 67% of 4-n-butyl-4'-methoxyazoxybenzene and 33% of 4-ethyl-4'-methoxyazoxybenzene has a nematic phase in the temperature range from $-5°$ to $+73°$ and a viscosity of $31.10^{-3}$ Pa.s at 20°.

A dielectric consisting of 95% of this two component mixture and 5% of p-(4-n-pentylcyclohexyl)-p'-ethoxybiphenyl has a nematic phase in the temperature range from $-10°$ to $+79°$ and a viscosity of $28.10^{-3}$ Pa.s at 20°.

EXAMPLE 8

A dielectric consisting of 67% of anisic acid 4-n-pentylphenyl ester and 33% of 4-n-hexyloxybenzoic acid 4'-n-pentylphenyl ester has a nematic phase in the temperature range from $+15°$ to $+48°$ and a viscosity of $58.10^{-3}$ Pa.s at 20°.

A dielectric consisting of 80% of this two-component mixture and 20% of p-(4-n-pentylcyclohexyl)-p'-ethylbiphenyl has a nematic phase in the temperature range from 0° to $+71°$ and a viscosity of $49.10^{-3}$ Pa.s at 20°.

EXAMPLE 9

A dielectric consisting of 77% of the two-component mixture according to Example 7 and 23% of p-(4-n-pentylcyclohexyl)-p'-ethylbiphenyl has a nematic phase in the temperature range from $-15°$ to $+95°$ and a viscosity of $30.10^{-3}$ Pa. at 20°.

EXAMPLE 10

A dielectric consisting of 80% of the two-component mixture of Example 8 and 20% of p-(4-n-hexylcyclohexyl)-p'-ethylbiphenyl has a nematic phase in the temperature range from 6° to 68° and a viscosity of $52.10^{-3}$ Pa.s at 20°.

EXAMPLE 11

A dielectric consisting of 29% of 4-(4-n-propylcyclohexyl)-benzonitrile, 41% of 4-(4-n-pentylcyclohexyl)-benzonitrile and 30% of 4-(4-n-heptylcyclohexyl)-benzonitrile has a nematic phase in the temperature range from −3° to +52° and a viscosity of 24 cSt at 20°.

A dielectric consisting of 74% of this ternary mixture and 26% of p-(4-n-pentylcyclohexyl)-p'-ethylbiphenyl has a nematic phase in the temperature range from −10° to +74° and a viscosity of 23 cSt at 20°.

EXAMPLE 12

The liquid crystal compound p-n-pentyl-p'-cyanobiphenyl has a nematic phase in the temperature range from 22.5° to 35° and a viscosity of 29.5 cSt at 20° (supercooled state).

A mixture of 90% of p-n-pentyl-p'-cyanobiphenyl and 10% of p-(4-n-pentylcyclohexyl)-p'-n-butylbiphenyl has a nematic phase in the temperature range from 18.5° to 49.2° and a viscosity of 29 cSt at 20°.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A cyclohexylbiphenyl of the formula

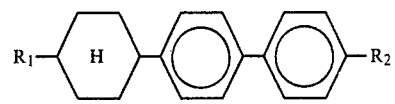

wherein $R_1$ is alkyl of 1–12 C atoms and $R_2$ is alkyl, alkoxy or alkanoyloxy each of 1–12 C atoms and each optionally perfluorinated.

2. A compound of claim 1 wherein $R_1$ is a $C_{2-8}$-straight chain alkyl.

3. A compound of claim 1 wherein $R_2$ is a $C_{2-8}$-alkyl, -alkoxy or -alkanoyl having a straight chain alkylene portion.

4. A liquid crystal dielectric, comprising at least two liquid crystal components, at least one being a compound of claim 1.

5. A liquid crystal dielectric of claim 4 having a negative dielectric anisotropy.

6. An electrooptical display element having a liquid crystal cell whose liquid crystal dielectric is that of claim 4.

7. A method of broadening the temperature range of the mesophase of a liquid crystal base material having negative anisotropy which comprises adding to the base material an amount of a compound of claim 1 effective to broaden its mesophase.

* * * * *